US007795231B2

(12) United States Patent
Bowman et al.

(10) Patent No.: US 7,795,231 B2
(45) Date of Patent: Sep. 14, 2010

(54) CONCENTRATED AQUEOUS AZALIDE FORMULATIONS

(75) Inventors: Lyle Bowman, Pleasanton, CA (US); S. Kumar Chandrasekaran, Moraga, CA (US); Roy Duane Archibald, Sonora, CA (US); Stephen Pham, Sacramento, CA (US); David Mufson, San Francisco, CA (US)

(73) Assignee: Insite Vision Incorporated, Alameda, CA (US)

( * ) Notice: Subject to any disclaimer, the term of this patent is extended or adjusted under 35 U.S.C. 154(b) by 0 days.

(21) Appl. No.: 11/905,854

(22) Filed: Oct. 4, 2007

(65) Prior Publication Data

US 2009/0093449 A1 Apr. 9, 2009

(51) Int. Cl.
*A61K 31/00* (2006.01)

(52) U.S. Cl. .......... 514/28

(58) Field of Classification Search .......... 514/28
See application file for complete search history.

(56) References Cited

U.S. PATENT DOCUMENTS

| | | | | |
|---|---|---|---|---|
| 6,239,113 | B1 * | 5/2001 | Dawson et al. | 514/29 |
| 6,514,945 | B1 * | 2/2003 | Boettner | 514/29 |
| 6,861,411 | B1 * | 3/2005 | Ahmed | 514/29 |
| 7,056,893 | B2 * | 6/2006 | Roy et al. | 514/29 |

OTHER PUBLICATIONS

Alvarez-Elcoro, S., M.D., et al., "The Macrolides: Erythromycin, Clarithromycin, and Azyithromycin," Mayo Clinic Proceedings, 1999, p. 613-634, vol. 74, Mayo Foundation for Medical Education and Research.

Ball, A. P., et al., "Azithromycin: an Interim Analysis," The Journal of International Medical Research, 1991, p. 446-450, vol. 19, Cambridge Medical Publications Ltd.

Blaug, S., Ph.D., Remington's Pharmaceutical Sciences, 1975, p. 1523-1553, 15th Ed., Ch. 87, Mack Publishing Company, Easton, Pa.

Girard, A. E., et al., "Pharmacokinetic and In Vivo Studies with Azithromycin (CP-62,993), a New Macrolide with an Extended Half-Life and Excellent Tissue Distribution," Antimicrobial Agents and Chemotherapy, Dec. 1987, p. 1948-1954, vol. 31, No. 12, American Society for Microbiology.

Gladue, R. P., et al., "In Vitro and In Vivo Uptake of Azithromycin (CP-62,993) by Phagocytic Cells: Possible Mechanism of Delivery and Release at Sites of Infection," Antimicrobial Agents and Chemotherapy, Mar. 1989, p. 277-282, vol. 33, No. 3, American Society for Microbiology.

Fiese et al., Comparison of the acid stability of azithromycin and erythromycin A., Journal of Antimicrobial Chemotherapy, Jan. 1990, vol. 25, Suppl A, p. 39-47, p. 39, para 2, 7 figs 4-5, table 3.

International Search Report and the Written Opinion of the International Searching Authority issued in Patent Application No. PCT/US08/70491 dated on Oct. 6, 2008.

* cited by examiner

*Primary Examiner*—Shaojia Anna Jiang
*Assistant Examiner*—Ganapathy Krishnan
(74) *Attorney, Agent, or Firm*—McDermott Will & Emery LLP

(57) ABSTRACT

The present invention relates to formulations of concentrated azalide antibiotics and methods for making and using them. Specifically, the invention relates to a method of treating an infection comprising administering to a patient in need thereof, an effective amount of a concentrated aqueous azalide antibiotic formulation made according to the method comprising dissolving an azalide antibiotic in an aqueous solution comprising a strong acid. The invention also relates to methods for making concentrated aqueous azalide antibiotic formulations for use in pulmonary infection, a nasopharyngeal infection, an otic infection, an ocular infection, a dermal or a vaginal infection. The invention also relates to concentrated aqueous azalide antibiotic formulations made by dissolving an azalide antibiotic in an aqueous solution comprising a strong acid.

8 Claims, 6 Drawing Sheets

Table 1: Ophthalmic Formulations

| Formulation Component | Formulation Composition | | | | | | |
|---|---|---|---|---|---|---|---|
| | **T01T** | **T02T** | **T03T** | **T04T** | **U01T** | **V04T** | **V05T** |
| EDTA | 0.1% | 0.1% | 0.1% | 0.1% | 0.1% | 0.1% | 0.1% |
| Sodium Chloride | 0.3% | 0.5% | 0.25% | 0.3% | 0.4% | 0.35% | 0.35% |
| Noveon AA-1 | 0.9% | 0.9% | 0.9% | 0.9% | 0.9% | 1.0% | 0.938% |
| Mannitol | 1.0% | 1.0% | 1.0% | 0.5% | 0.8% | 0.8% | 0.8% |
| Benzalkonium Chloride | 0.01% | 0.01% | 0.01% | 0.01% | 0.01% | 0.01% | 0.01% |
| Sodium Citrate Dihydrate | 0.3% | 0.1% | 0.1% | 0.1% | 0.1% | 0.1% | 0.1% |
| Citric Acid | 0.2% | 0.2% | 0.2% | 0.2% | 0.2% | 0.2% | 0.2% |
| Poloxamer 407 | 0.2% | 0.2% | 0.2% | 0.2% | 0.2% | 0.2% | 0.2% |
| Azithromycin | 2.1% | 2.1% | 3.1% | 3.1% | 2.1% | 2.2% | 2.2% |
| HCl (6N) | N/A | 0.5% | 0.9% | 1.0% | 0.5% | 0.5% | 0.5% |
| NaOH (2N) | 5.1% | 4.9% | 5.0% | 5.1% | 4.9% | 5.3% | 5.3% |
| Dexamethasone | 0.1% | | | | | | |

Table 2 Otic Formulations

| Formulation Component | Formulation Composition | | | | | | | |
|---|---|---|---|---|---|---|---|---|
| | U02T | U03T | U04T | V01T | V01T | V01T | V02T | V03T |
| EDTA | 0.1% | 0.1% | 0.1% | 0.1% | 0.1% | 0.1% | 0.1% | 0.1% |
| Sodium Chloride | 0.3% | 0.3% | 0.2% | 0.3% | 0.4% | 0.5% | 0.5% | 0.5% |
| Noveon AA-1 | 0.5% | 0.5% | 0.6% | 0.6% | 0.6% | 0.6% | 0.5% | 0.6% |
| Mannitol | 0.5% | 0.5% | 0.5% | 0.5% | 0.5% | 0.5% | 0.5% | 0.5% |
| Benzalkonium Chloride | 0.01% | 0.01% | 0.01% | 0.01% | 0.01% | 0.01% | 0.01% | 0.01% |
| Sodium Citrate Dihydrate | 0.1% | 0.1% | 0.1% | 0.1% | 0.1% | 0.1% | 0.1% | 0.1% |
| Citric Acid | 0.4% | 0.4% | 0.2% | 0.2% | 0.2% | 0.2% | 0.2% | 0.2% |
| Poloxamer | 0.2% | 0.2% | 0.2% | 0.2% | 0.2% | 0.2% | 0.2% | 0.2% |
| Azithromycin | 3.1% | 3.1% | 3.2% | 2.0% | 2.0% | 2.0% | 2.0% | 2.0% |
| HCl (6N) | 1.0% | 1.0% | 1.0% | 0.5% | 0.5% | 0.5% | 0.5% | 0.5% |
| NaOH (2N) | 5.0% | 2.9% | 2.8% | 3.0% | 3.0% | 3.0% | 2.5% | 2.9% |
| Dexamethasone | 0.1% | 0.1% | 0.1% | 0.1% | 0.1% | 0.1% | 0.1% | 0.1% |

Table 3: Nasal Formulations

| Formulation Component | Function | Concentration w/w% | Concentration w/w% | Concentration w/w% | Concentration w/w% |
|---|---|---|---|---|---|
| Formulation | | 1 | 2 | 3 | 4 |
| Azithromycin monohydrate | Active ingredient | 3.0 | 3.0 | 2.0 | 2.0 |
| Dexamethasone | Active ingredient | 0.1 | | 0.1 | |
| Polycarbophil | Suspending agent/mucoadhesive agent | 0.525 | 0.525 | 0.525 | 0.525 |
| Hydrochloric acid (1N) | pH adjusting agent | 6 | 6 | 3 | 3 |
| Dextrose | Osmolality adjusting agent | 0.5 | 0.5 | 0.5 | 0.5 |
| Polysorbate 80 | Surfactant | 0.01 | 0.01 | 0.01 | 0.01 |
| EDTA | Chelator | 0.1 | 0.1 | 0.1 | 0.1 |
| Citric acid | pH buffer | 0.2 | 0.2 | 0.2 | 0.2 |
| Sodium citrate dihydrate | pH buffer | 0.14 | 0.14 | 0.14 | 0.14 |
| Benzalkonium chloride | Preservative | 0.011 | 0.011 | 0.011 | 0.011 |
| Sodium chloride | Osmolality adjusting agent | 0.3 | 0.3 | 0.3 | 0.3 |
| Sodium hydroxide | pH adjusting agent | q.s. to pH 6.3 | q.s. to pH 6.3 | q.s. to pH 6.3 | q.s. to pH 6.3 |
| Purified Water | Diluent | q.s. to 100% | q.s. to 100% | q.s. to 100% | q.s. to 100% |

Table 4: Inhalation Formulations

| Formulation Component | Function | Concentration w/w% | Concentration w/w% | Concentration w/w% | Concentration w/w% |
|---|---|---|---|---|---|
| Formulation | | 1 | 2 | 3 | 4 |
| Azithromycin monohydrate | Active ingredient | 3.0 | 3.0 | 2.0 | 2.0 |
| Dexamethasone | Active ingredient | 0.1 | | 0.1 | |
| Polycarbophil | Suspending agent/mucoadhesive agent | 0.525 | 0.525 | 0.525 | 0.525 |
| Hydrochloric acid (1N) | pH adjusting agent | 6 | 6 | 3 | 3 |
| Dextrose | Osmolality adjusting agent | 0.5 | 0.5 | 0.5 | 0.5 |
| Polysorbate 80 | Surfactant | 0.01 | 0.01 | 0.01 | 0.01 |
| EDTA | Chelator | 0.1 | 0.1 | 0.1 | 0.1 |
| Citric acid | pH buffer | 0.2 | 0.2 | 0.2 | 0.2 |
| Sodium citrate dihydrate | pH buffer | 0.14 | 0.14 | 0.14 | 0.14 |
| Benzalkonium chloride | Preservative | 0.011 | 0.011 | 0.011 | 0.011 |
| Sodium chloride | Osmolality adjusting agent | 0.3 | 0.3 | 0.3 | 0.3 |
| Sodium hydroxide | pH adjusting agent | q.s. to pH 6.3 | q.s. to pH 6.3 | q.s. to pH 6.3 | q.s. to pH 6.3 |
| Purified Water | Diluent | q.s. to 100% | q.s. to 100% | q.s. to 100% | q.s. to 100% |

Table 5: Dermal Formulations

| Formulation Component | Function | Concentration w/w% | Concentration w/w% | Concentration w/w% | Concentration w/w% |
|---|---|---|---|---|---|
| Formulation | | 1 | 2 | 3 | 4 |
| Azithromycin monohydrate | Active ingredient | 3.0 | 3.0 | 2.0 | 2.0 |
| Dexamethasone | Active ingredient | 0.1 | | 0.1 | |
| Polycarbophil | Suspending agent/mucoadhesive agent | 3.0 | 3.0 | 3.0 | 3.0 |
| Hydrochloric acid (1N) | pH adjusting agent | 6 | 6 | 3 | 3 |
| Cab-O-Sil | Structure Agent | 1.0 | 1.0 | 1.0 | 1.0 |
| Dextrose | Osmolality adjusting agent | 0.5 | 0.5 | 0.5 | 0.5 |
| Polysorbate 80 | Surfactant | 0.01 | 0.01 | 0.01 | 0.01 |
| EDTA | Chelator | 0.1 | 0.1 | 0.1 | 0.1 |
| Citric acid | pH buffer | 0.2 | 0.2 | 0.2 | 0.2 |
| Sodium citrate dihydrate | pH buffer | 0.14 | 0.14 | 0.14 | 0.14 |
| Benzalkonium chloride | Preservative | 0.011 | 0.011 | 0.011 | 0.011 |
| Sodium chloride | Osmolality adjusting agent | 0.3 | 0.3 | 0.3 | 0.3 |
| Sodium hydroxide | pH adjusting agent | q.s. to pH 6.3 | q.s. to pH 6.3 | q.s. to pH 6.3 | q.s. to pH 6.3 |
| Purified Water | Diluent | q.s. to 100% | q.s. to 100% | q.s. to 100% | q.s. to 100% |

Table 6: Peridontal Formulations

| Formulation Component | Function | Concentration w/w% | Concentration w/w% | Concentration w/w% | Concentration w/w% |
|---|---|---|---|---|---|
| Formulation | | 1 | 2 | 3 | 4 |
| Azithromycin monohydrate | Active ingredient | 3.0 | 3.0 | 2.0 | 2.0 |
| Dexamethasone | Active ingredient | 0.1 | | 0.1 | |
| Polycarbophil | Suspending agent/mucoadhesive agent | 1.5 | 1.5 | 1.5 | 1.5 |
| Hydrochloric acid (1N) | pH adjusting agent | 6 | 6 | 3 | 3 |
| Dextrose | Osmolality adjusting agent | 0.5 | 0.5 | 0.5 | 0.5 |
| Poloxamer 407 | Surfactant | 0.01 | 0.01 | 0.01 | 0.01 |
| EDTA | Chelator | 0.1 | 0.1 | 0.1 | 0.1 |
| Citric acid | pH buffer | 0.2 | 0.2 | 0.2 | 0.2 |
| Sodium citrate dihydrate | pH buffer | 0.14 | 0.14 | 0.14 | 0.14 |
| Benzalkonium chloride | Preservative | 0.01 | 0.01 | 0.01 | 0.01 |
| Sodium chloride | Osmolality adjusting agent | 0.3 | 0.3 | 0.3 | 0.3 |
| Sodium hydroxide | pH adjusting agent | q.s. to pH 6.3 | q.s. to pH 6.3 | q.s. to pH 6.3 | q.s. to pH 6.3 |
| Purified Water | Diluent | q.s. to 100% | q.s. to 100% | q.s. to 100% | q.s. to 100% |

CONCENTRATED AQUEOUS AZALIDE FORMULATIONS

FIELD OF THE DISCLOSURE

The present invention relates to formulations of concentrated azalide antibiotics and methods for making and using them.

BACKGROUND OF THE INVENTION

The human body is susceptible to bacterial and parasitic infections arising from both traumatic and non-traumatic related events. Infections are a concern after surgery, and precautions are correspondingly taken to prevent the onset of infection. However, even without the invasive trauma of a surgical procedure, infections in the eye, ears, mouth, skin and other superficial tissues can occur.

Treating infections in superficial tissues can be challenging and/or problematic because of the difficulty in delivering an antibiotic to the affected tissue. The simple and direct approach of topically applying the antibiotic has several benefits, including the avoidance of side effects, bypassing the hepatic first pass, and the reduced chance of developing resistant strains of bacteria as compared to systemic administration. However, for a variety of reasons, many antibiotics are not amenable or suitable for topical application.

For example, in order for a topical application to be effective, the antibiotic must be able to penetrate the desired tissue. Also, the permeability must be sufficient to impart an effective dose. Many drugs do not possess a requisite solubility or permeability with regard to superficial tissues. It should be noted that the permeability of the superficial tissues are quite different from that of the tissues encountered in the stomach and intestinal tract. Thus, while a certain drug may be readily absorbed in the intestines and introduced into the blood supply for systemic administration, the same drug may be incapable of being absorbed by or passing through the substantially avascular outer layers of superficial tissues at a minimally acceptable therapeutic concentration. Moreover, the mechanism of transport or uptake of the drug is entirely different for topical administration than for oral administration.

Azithromycin (U.S. Pat. No. 4,517,359) is a well-known antibiotic belonging to the macrolide class (of which erythromycin is the precursor). Notwithstanding the structural similarity, azithromycin can be considered as unique within the macrolides class, such as to be included in a new class of antibiotics known as azalides. In particular, the specific characteristics of azithromycin make this molecule more stable, tolerated and effective than its precursor erythromycin (S. Alvarez-Elcoro, M. J. Enzler, "The macrolides: Erythromycin, clarithromycin, and azithromycin", Mayo. Clinic Proceeding, 1999, 74: 613-634).

Azithromycin, even in comparison to other recent macrolides, shows a superior antibacterial activity against some gram-negative organisms, while retaining the same efficacy against gram-positive organisms. Moreover azithromycin has an extensive intracellular distribution into specific tissues after oral administration [R. P. Glaude et al., Antimicrob. Agents and Chemother., 1989, 33(3): 277-82]. The extended half-life of azithromycin makes it potentially suitable for once-daily administration against infections of the respiratory tract, skin and soft tissues [A. P. Ball et al., J. Int. Med. Res., 1991, 19(6): 446-50; A. E. Girard et al., Antimicrob. Agents and Chemother., 1987, 31(12): 1948-1954].

Efficient methods for preparing high concentration and well tolerated aqueous azalide formulations have been elusive. Generally, azalide antibiotics are poorly soluble in water. The aqueous solubility at pH 7.4 at 37° C. is 39 mg/ml. Aqueous solubility can be improved when the antibiotic is converted to a salt form. For example, azithromycin dihydrochloride has good water solubility. However, there are potential safety problems associate with the topical use of its salts.

U.S. Pat. No. 6,277,829 discloses a process for the preparation of an aqueous ophthalmic formulation containing azithromycin which comprises the ophthalmically acceptable polybasic phosphate in a concentration range from 7.8 to 68.6 g/l, citric acid monohydrate in an amount ranging from 0.9 to 35.94 g/l, and azithromycin in an amount ranging from 0.1 to 100 g/l, within a temperature range from 15 to 25° C., wherein the molar ratio of azithromycin to citric acid is about 1:0.67 to 1:1.5; wherein pH is adjusted to a value of 5.5-7.6, and up to a final osmolality between about 130 to about 300 mOsm/Kg. However, these solutions utilize phosphate buffer system comprising of phosphoric acid in combination with a polymeric suspending agent with increased residence time can be irritating to the eye. Additionally, phosphate buffered system can promote fungus growth in the formulation.

As such there remains a need for concentrated yet well tolerated aqueous formulations of azalide antibiotics for topical application.

All documents scientific and patent, cited herein are incorporated by reference in their entirety.

SUMMARY OF THE DISCLOSURE

The present invention relates to aqueous formulations of azalide antibiotics. Such formulations can be topically administered to a variety of tissues either prophylactically or to treat bacterial or parasitic infections of susceptible organisms. Topical routes of administration include but are not limited to oral, otic, ophthalmic, dermal, periodontal, vaginal, respiratory and nasal.

The present invention includes and provides a topical composition comprising water and an azalide antibiotic; wherein said composition has a pH of about 6.0 to about 7.0. The present invention also includes and provides an formulations comprising about 0.1% to about 1.0% sodium chloride; about 0.1% to about 1.0% citric acid; about 0.1% to about 2.0% sodium citrate, about 2% to about 30.0% azithromycin, more preferably about 2% to about 20%, most preferably about 2% to about 10% and even more preferably about 2% to about 5%; wherein the composition has a pH of about 6.0 to about 7.0 or more preferably from a pH of about 6.0 to about 6.5, most preferably about 6.1 to about 6.4 and even more preferably about 6.2 to about 6.3.

One aspect of the invention relates to a method of treating an infection comprising administering to a patient in need thereof, an effective amount of a concentrated aqueous azalide antibiotic formulation made according to the method comprising dissolving an azalide antibiotic in an aqueous solution comprising a strong acid. In one embodiment the azalide antibiotic is azithromycin. In another embodiment of this aspect of the invention, the aqueous azalide antibiotic formulation has about 2% azithromycin. In a further embodiment, the aqueous azalide antibiotic formulation has about 3% azithromycin. In yet another embodiment, the aqueous azalide antibiotic formulation has about 4% azithromycin. In still another embodiment, the aqueous azalide antibiotic formulation has about 5% azithromycin. In still a further embodiment, the strong acid is hydrochloric acid. In yet a further embodiment, the aqueous solution has a pH of about 5 to about 6. In still a further embodiment, the pH is about 5.5 to about 6. In yet another embodiment, the aqueous solution comprises citrate and citric acid. In yet a further embodiment, the method further comprises the step of adding to the aqueous solution a second solution comprising a strong base. In another embodiment, the strong base is sodium hydroxide. In still another embodiment, the second solution is added in an amount sufficient to bring the combined solutions to a pH from about 6 to about 7. In still another embodiment, the second solution is added in an amount sufficient to bring the combined solutions to a pH from about 6.2 to about 6.5. In still another embodiment, the second solution is added in an amount sufficient to bring the combined solutions to a pH from about 6.3. In yet a further embodiment, the second solution comprises a polymeric agent. In still a further embodiment, the polymeric agent is Noveon AA-1. In another embodiment, the aqueous azalide antibiotic formulation comprises an anti-inflammatory agent. In a further embodiment, the anti-inflammatory agent is a dexamethasone. In yet another embodiment, the dexamethasone is at a concentration of about 0.1% and wherein the azalide antibiotic is azithromycin at a concentration of about 3%. In another embodiment, the infection a pulmonary infection, a nasopharyngeal infection, an otic infection, an ocular infection, a dermal or a vaginal infection.

Another aspect of the invention relates to a method of making a concentrated aqueous azalide antibiotic formulation comprising dissolving an azalide antibiotic in an aqueous solution comprising a strong acid according to the aforementioned methods.

Yet another aspect of the invention relates to a topical aqueous azalide antibiotic formulation made by the method comprising dissolving an azalide antibiotic in an aqueous solution comprising a strong acid according to the aforementioned methods.

Another aspect of the invention relates to a method for making an aqueous azalide antibiotic formulation comprising: dissolving an azalide antibiotic in a first aqueous solution comprising a strong acid and adding to the aqueous solution comprising the azalide antibiotic a second solution comprising a strong base in an amount sufficient to bring the pH of the aqueous solution comprising the azalide antibiotic to about 6 to about 7, to obtain an aqueous azalide antibiotic formulation. In one embodiment of this aspect of the invention, the azalide antibiotic is azithromycin. In another embodiment, the first aqueous solution is buffered. In yet another embodiment, the first aqueous solution comprises sodium citrate and citric acid. In still a further embodiment, the second solution comprises a polymeric agent. In yet another embodiment, the second aqueous solution comprises a crosslinked carboxyvinyl polymer. In still another embodiment, the second solution comprises Noveon AA-1. In yet another embodiment, the strong acid is hydrochloric acid. In yet a further embodiment, the first aqueous solution has a pH of about 5 to about 6. In still a further embodiment, the strong base is sodium hydroxide. In another embodiment, the aqueous azalide antibiotic formulation has about 2% to about 10% azithromycin. In yet a further embodiment, the aqueous azalide antibiotic formulation has about 2% to about 5% azithromycin. In another embodiment, the aqueous azalide antibiotic formulation has a pH of about 6 to about 7. In a further embodiment, the aqueous azalide antibiotic formulation has a pH of about 6.2 to about 6.8. In yet a further embodiment, the aqueous azalide antibiotic formulation has a pH of about 6.2 to about 6.5. In still another embodiment, the aqueous azalide antibiotic formulation has a pH of about 6.3. In still another embodiment, the aqueous azalide antibiotic formulation has an osmolality of about 300 mOsm/kg. In still another embodiment, the aqueous azalide antibiotic formulation comprises an anti-inflammatory agent. In yet another embodiment, the anti-inflammatory agent is dexamethasone.

Another aspect of the invention relates to a topical antibiotic formulation comprising the aqueous azalide antibiotic formulation made according to the method comprising dissolving an azalide antibiotic in a first aqueous solution comprising a strong acid and having a pH of about 6 and adding to the aqueous solution comprising the azalide antibiotic a second solution comprising a strong base in an amount sufficient to bring the pH of the aqueous solution comprising the azalide antibiotic to about 6 to about 7, to obtains an aqueous azalide antibiotic formulation. In one embodiment of this aspect of the invention, the topical antibiotic formulation is an otic formulation. In another embodiment, the topical antibiotic formulation is an ophthalmic formulation. In another embodiment, the topical antibiotic formulation is a nasal formulation. In another embodiment, the topical antibiotic formulation is a dermal formulation. In another embodiment, the topical antibiotic formulation is a periodontal formulation. In another embodiment, the topical antibiotic formulation is an inhalational formulation. In another embodiment, the topical antibiotic formulation is a vaginal formulation.

Another aspect of the invention relates to method of treating an infection comprising administering to a patient in need thereof, an effective amount of the aqueous azalide antibiotic formulation made according to the methods disclosed herein. In one embodiment of this aspect of the invention, the infection is an otic infection. In another embodiment, the infection is an ophthalmic infection. In another embodiment, the infection is a nasopharyngeal infection. In another embodiment, the infection is a dermal infection. In another embodiment, the infection is a periodontal or oral infection. In another embodiment, the infection is a vaginal infection. Yet in another embodiment, the infection is a pulmonary infection.

Additional advantages of the present disclosure will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. The present invention may be practiced without some or all of these specific details. In other instances, well known process operations have not been described in detail to avoid unnecessarily obscure the present disclosure. Accordingly, the description is to be regarded as illustrative in nature, and not as restrictive.

BRIEF DESCRIPTION OF THE DRAWINGS

Table 1 describes exemplary ophthalmic formulation compositions with respect to the percentage of various formulation components.

Table 2 describes exemplary otic formulation compositions with respect to the percentage of various formulation components.

Table 3 describes exemplary nasal formulation compositions with respect to the percentage of various formulation components.

Table 4 describes exemplary inhalation formulation compositions with respect to the percentage of various formulation components.

Table 5 describes exemplary dermal formulation compositions with respect to the percentage of various formulation components.

Table 6 describes exemplary periodontal formulation compositions with respect to the percentage of various formulation components.

DETAILED DESCRIPTION OF THE DISCLOSURE

Azalides are a known subclass of macrolide antibiotics. For the present invention and as used in this specification, an "azalide antibiotic" means a derivitized erythromycin A structure having a nitrogen atom inserted into the lactone ring. Additional variations from the erythromycin structure are also embraced within the term "azalide antibiotic." Such additional variations include the conversion of a hydroxyl group to an alkoxy group, especially methoxy (so-called "O-methylated" forms), for example at the 6 and/or 12 position. Such compounds are described in U.S. Pat. No. 5,250,518. Other variations relate to derivatives of the sugar moieties, for example, 3' desmethoxy derivatives and the formation of oxo or oxime groups on the sugar ring such as at the 4' position as described in U.S. Pat. No. 5,441,939. This patent also teaches that the adjacent hydroxyl groups at the 11 and 12 position of the lactone ring can be replaced with a single carbonate or thiocarbonate group. In short, an azalide antibiotic for purposes of the present invention is any derivative of the erythromycin structure that contains a 15-member lactone ring having a ring nitrogen, preferably at the 9 position, and a sugar group attached via a glycosidic bond to the lactone ring at the 5 position and at the 3 position, and which still exhibits bacteriostatic or bactericidal activity.

Preferred azalide antibiotics are represented by formula (I) and pharmaceutically acceptable salts thereof.

(I)

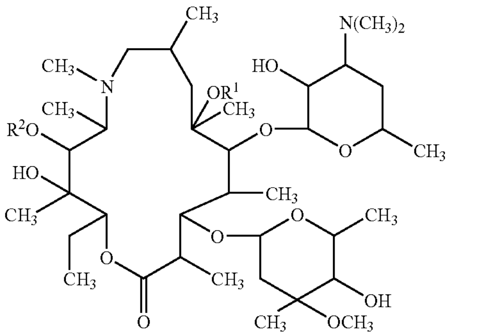

wherein $R^1$ and $R^2$ each independently represent a hydrogen atom or methyl group.

Preferably at least one of $R^1$ and $R^2$ is a hydrogen atom. Azithromycin, the common name for N-methyl-11-aza-10-deoxo-10-dihydroerythromycin, corresponds to the compound of formula (I) where both $R^1$ and $R^2$ are hydrogen atoms. Azithromycin was disclosed in U.S. Pat. Nos. 4,474,768 and 4,517,359, and is the most preferred azalide antibiotic. In particular, the monohydrate form of azithromycin is especially contemplated for use in the present invention, although other forms are also suitable.

Azithromycin has been used as an oral antibiotic and is sold worldwide under the brand name Zithromax™ by Pfizer Inc. Azithromycin is a broad spectrum antibiotic that is generally more effective in vitro than erythromycin. Moreover, because azithromycin is an azalide and thus has a ring nitrogen atom, it exhibits improved acid-stability, half-life, and cellular uptake in comparison to erythromycin. The high uptake and retention of azithromycin into cells, including phagocytic blood cells, allows systemically administered azithromycin to be nonetheless preferentially delivered to the site of the infection. The mechanism has been reported to be as follows. The ingested azithromycin is absorbed through the intestine into the blood stream from which it enters most cells of the body including, inter alia, the white blood cells. In response to an infection within the body, white blood cells, including those containing azithromycin, are attracted to the infectious site. When the white blood cells die, the azithromycin is released. As more and more white blood cells arrive at the infectious site and die, the concentration of azithromycin in the surrounding tissue increases, eventually surpassing the minimum inhibitory concentration (MIC). Once at the infectious site, the azithromycin remains in the tissue for a prolonged period of time. Due to its long half-life, an effective concentration of azithromycin is present at the infected site for many days after cessation of administration. While typically administered via the oral route, Azalide antibiotics are also amenable to topical and parenteral administrations.

One aspect of the invention relates to methods of preparing a concentrated aqueous azalide antibiotic formulation. The process generally involves dissolving an azalide antibiotic in a strongly acidic aqueous and preferably a buffered solution, and then adding a strong bases to the solution and adjusting the pH to about 6.0 to about 7.0, more preferably from about 6.0 to about 6.6, more preferably of about 6.2 to about 6.4, more preferably of about 6.25 to 6.35, and even more preferably about 6.3. Previously, azithromycin antibiotics has been discovered to have a maximum stability over a pH interval of about 6.0 to about 7.0; preferably with a maximum at a pH of about 6.3 (See U.S. Pat. No. 7,056,893). Given this teaching, the skilled artisan would have sought to avoid pH ranges below 6 and above 7 when formulating aqueous formulations of azalide antibiotics. However, it was surprisingly discovered that concentrated aqueous azalide antibiotic formulations can be made by dissolving the azalide antibiotic in a strong acid and then bringing the pH to a range of about 6.0 to about 7.0 with a base. Notwithstanding concerns that the strongly acidic conditions would cause degradation of the azalide antibiotic, it was found that dissolving azalide antibiotic in a strong acid and subsequent pH adjustment did not have a deteriorative effect on the azalide antibiotic.

The term "concentrated" aqueous azalide antibiotic formulation refers to an aqueous solution of an azalide antibiotic having a concentration of about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% about 21%, about 22%, about 23%, about 24%, about 25%, about 26% about 27%, about 28%, about 29% or about 30%. Preferably, the concentrated formulation is about 1% to about 30%, 2% to about 25%, about 2% to about 20%, more preferably about 2% to about 8%.

"Strong acid" as used herein refers to an acid that dissociates completely in an aqueous solution (not in the case of sulfuric acid as it is diprotic), or in other terms, with of about pKa<−1.74. This generally means that in aqueous solution at standard temperature and pressure, the concentration of hydronium ions is equal to the concentration of strong acid introduced to the solution. The preferred strong acids include but are not limited to sulfuric, acetic, nitric, and perchloric acids. The most preferred strong acid is hydrochloric acid.

"Strong base" as used herein refers to a basic chemical compound that is able to deprotonate very weak acids in an acid-base reaction. Preferably, such compounds have a pKa of more than about 13. Common examples of strong bases are the hydroxides of alkali metals and alkaline earth metals like NaOH. Very strong bases are even able to deprotonate very weakly acidic C—H groups in the absence of water. Strong bases include but are not limited to potassium hydroxide, barium hydroxide, cesium hydroxide, sodium hydroxide, strontium hydroxide, lithium hydroxide and rubidium hydroxide. The preferred strong base is NaOH.

Although azithromycin can reach many of tissues by oral administration, it has been discovered that azalide antibiotics in general and azithromycin in particular are amenable to topical administration. U.S. Pat. Nos. 6,239,113, 6,569,443, 7,056,893, all of which are incorporated by reference in their entirety.

"Topical administration" refers to a route of administration which is the path by which the azalide antibiotic is brought into contact with the body. Preferably, in topical administration the effect of the azalide antibiotic is local and the composition is applied directly where its action is desired. Topical application is application directly to superficial tissues such as for example in tact or compromised skin (epicutaneous/dermal), tissues of the mouth (buccal/periodontal), airway and lungs (inhalation), rectal (by enema), eye (ocular), ear (otic), nose (intranasal), and vagina (vaginal). Preferably, topical application is to mucous membrane, also called mucosa, lining all body passages that communicate with the exterior such as the respiratory, genitourinary, and alimentary tracts, and having cells and associated glands that secrete mucus.

A multitude of appropriate topical formulations can be found in the formulary known to all pharmaceutical chemists: Blaug, S., Ch. 87 in Remington's Pharmaceutical Sciences (15th Ed., 1975, Mack Publishing Company, Easton, Pa. 18042). These compositions include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. Preferred formulations of the invention are concentrated aqueous azalide antibiotic for otic, dermal, ophthalmic, nasal, pulmonary, vaginal or periodontal administration.

The preferred formulations of the invention may be formulated as drops, sprays, ointments, creams, lotions, gels, emulsions or other aqueous solutions or dispersions. Preferably, the primary vehicle is water or a biocompatible solvent that is substantially neutral or that has been rendered substantially neutral. The liquid vehicle can include other materials, such as alcohols, glycerin, polyethylene glycol, and mineral oils with various emulsifiers or dispersing agents as known in the art to obtain the desired pH, consistency and viscosity. In a further embodiment, the composition is an irrigating solution for use in a process of irrigating a surgical site.

The amount of azalide antibiotic topically supplied is preferably effective to treat or prevent infection in a superficial tissue. This means that the conditions of application result in a retardation or suppression of the infection. Typically at least about $MIC_{90}$ for the targeted bacteria or parasite is delivered to the target tissue by the topical application of an effective amount. More concretely, the concentration within the tissue is desired to be at least about 1 μg/g, preferably at least about 10 μg/g, and more preferably at least about 20 μg/g. The amount of azalide actually applied to the tissue surface will almost always be higher than the tissue concentration. This reflects the permeability of the azalide antibiotic through the outer layers of the tissue and that penetration is, to some extent, concentration gradient. Thus, applying greater amounts to the exterior will drive more antibiotic into the tissues. Delivery of formulations as a depot will advantageously maintain the concentration of the azalide antibiotic in the affected tissues at or above the $MIC_{90}$ for a period of at least about 2 hours, or more preferably at least about 4 hours, more preferably at least about 8 hours, or more preferably at least about 12 hours and more preferably at least 18 hours.

Where a series of applications are typically employed in a topical administration dosing regimen, it is possible that one or more of the earlier applications will not achieve an effective concentration in the tissue, but that a later application in the regimen will achieve an effective concentration. This is contemplated as being within the scope of topically applying an azalide antibiotic in an effective amount.

The concentration of azalide antibiotic present in the inventive formulations depends upon the dosage form, the release rate, the dosing regimen, and the location and type of infection. Generally speaking, the concentration is from about 2% to about 12.0% although it is possible to prepare and utilize formulations with higher concentrations of azalide antibiotics such as 15%, 20%, 25% or even about 30%. In one embodiment of the invention, the concentration is about 2% to about 20%. In another embodiment of the invention, the concentration is about 2% to about 10%. In another embodiment of the invention, the concentration is about 2% to about 5%. In another embodiment of the invention, the concentration is about 2% to about 3%. In another embodiment of the invention, the concentration is about 2% to about 2.5%.

Azalide antibiotic formulations of this invention suitable for topical administration may include one or more "pharmaceutically acceptable carriers," such as for example an otically, ophthalmically, dermally, nasally, pulmonary, vaginally or buccally acceptable carrier. Typically the pharmaceutically acceptable carriers are aqueous-based solution or suspension. Generally, azalide antibiotics are poorly soluble in water. However, the methods disclosed herein overcome this problem and allow for the preparation of concentrated azalide antibiotic formulations.

The aqueous formulations (solutions or suspensions) for use in the present invention preferably use water that has no physiologically harmful constituents. Typically purified or deionized water is used. The pH is adjusted by adding any physiologically and acceptable pH adjusting acids, bases, or buffers to within the range of about 5.0 to about 7.0, more preferably from about 5.8 to about 6.8, more preferably about 6.0 to about 6.5, more preferably at a pH of about 6.2 to about 6.4, more preferably about 6.25 to about 6.35, or even more preferably about 6.3. Any of the aforementioned ranges can be used with any of the formulations of the present invention, including, without limitation. Examples of acids include acetic, boric, citric, lactic, hydrochloric, and the like, and examples of bases include potassium hydroxide, sodium hydroxide, sodium borate, sodium citrate, sodium acetate, sodium lactate, tromethamine, THAM (trishydroxymethylamino-methane), and the like. Salts and buffers include but are not limited to citrate/dextrose, sodium bicarbonate, ammonium chloride and mixtures of the aforementioned acids and bases. The pH is preferably adjusted by adding sodium hydroxide. The preferred buffer is citric acid and amounts of citric acid of about 0.01% to about 5% by weight, preferably about 0.05% to about 0.4% by weight, based on the total weight of the composition, are typically used.

The formulations of the present invention suitable for topical administration, including both ointments and suspensions, have a viscosity that is suited for the selected route of administration. Such viscosity enhancing agents include, for example, polyvinyl alcohol, polyvinyl pyrrolidone, povidone, polyethylene glycol, Carbomer 940/934P, methyl cellulose, hydroxypropyl methylcellulose, hydroxyethyl cellulose, carboxymethyl cellulose. The azalide antibiotic formulations of the instant invention containing aqueous polymeric suspensions may be formulated so that they retain the same or substantially the same viscosity that they had prior to administration to the tissue. Alternatively, in preferred embodiments for they may be formulated so that there is increased gelation upon contact with a superficial tissue or bodily fluid, e.g., tears.

The osmotic pressure ($\pi$) of the aqueous composition of this invention is generally from about 10 milliosmolar (mOsM) to about 400 mOsM, more preferably from about 260 to about 340 mOsM and most preferably about 280 to about 320 or about 300 mOsM. If necessary, the osmotic pressure can be adjusted by using appropriate amounts of physiologically acceptable salts or excipients. Sodium chloride is preferred to approximate physiologic fluid, and amounts of sodium chloride from about 0.01% to about 0.9% by weight, and preferably from about 0.1% to about 0.9% by weight, and more preferably about 0.2% to about 0.5% by weight based on the total weight of the composition, are typically used. Equivalent amounts of one or more salts made up of cations such as potassium, ammonium and the like and anions such as chloride, citrate, ascorbate, borate, bicarbonate, sulfate, thiosulfate, bisulfate, sodium bisulfate, ammonium sulfate, and the like can also be used in addition to or instead of sodium chloride to achieve osmolalities within the above-stated range. Similarly, a sugar such as mannitol, dextrose, sorbitol, glucose and the like can also be used to adjust osmolality.

The solubility of the components of the present formulations may also be enhanced by a surfactant or other appropriate co-solvent in the composition or solubility enhancing agents like cyclodextrins such as hydroxypropyl, hydroxyethyl, glucosyl, maltosyl and maltotriosyl derivatives of alpha-, beta-, and gamma-cyclodextrin. A particularly preferred solubility enhancer is hydroxypropyl-beta cyclodextrin (HPBC). In one embodiment, the composition comprises 0.1% to 20% hydroxypropyl-beta-cyclodextrin, more preferably 1% to 15% hydroxypropyl-beta-cyclodextrin, and even more preferably from 2.5% to 10% hydroxypropyl-beta-cyclodextrin. Co-solvents include polysorbates (for example, polysorbate 20, 60, and 80), polyoxyethylene/polyoxypropylene surfactants (e.g., Pluronic F-68, F 84 and P-103), cyclodextrin, fatty-acid glycerol-polyethylene glycol esters, other solubilizing agents such as Octoxynol 40, Tyloxapol and Pluronics, or other agents known to those skilled in the art and mixtures thereof. The amount of solubility enhancer used will depend on the amount of azalide antibiotic in the composition, with more solubility enhancer used for greater amounts of azalides. Typically solubility enhancers are employed at a level of from 0.01% to 20% by weight depending on the ingredient. Preferable ranges are 1% to 5% and 0.1% to 2%. Wetting agents include polyvinyl pyrolidone, polyvinyl alcholol, polyethylene glycol. The solubilizing agents may help keep the other components of the topical composition in solution, including the azalide antibiotic in solution. The wetting agent helps the formulation to spread over the tissue.

If necessary, free divalent metal ions may be removed from the solution by using appropriate amounts of a chelating agent. EDTA disodium is preferred to remove excess free metal ions. Citric acid is another preferred chelating agent. The amounts of citric acid of about 0.01% to about 1% by weight, preferably about 0.05% to about 0.5% by weight, and more preferably about 0.1% to about 0.2% by weight based on the total weight of the composition, are typically used. In addition to EDTA and citric acid, other chelating agents including organic phosphonic acids such as Dequest 2060 may also be employed. Useful phosphonic include, but are not limited to diethylene triamine penta(methylene-phosphonic acid) and the like which are commercially available from Monsanto under the DEQUEST brand name.

The inventive formulations may contain one or more of the following: surfactants, adjuvants including additional medicaments, buffers, antioxidants, tonicity adjusters, preservatives, thickeners or viscosity modifiers, and the like. Additives in the formulation may include sodium chloride, EDTA (disodium edetate), and/or BAK (benzalkonium chloride), sorbic acid, methyl paraben, propyl paraben, chlorhexidine, and sodium perborate. Suitable preservatives also include: polyquaternium-1, thimerosal, chlorobutanol, methyl paraben, propyl paraben, phenylethyl alcohol, sorbic acid, or other agents known to those skilled in the art. Typically such preservatives are employed at a level of from 0.001% to 1.0% by weight.

The formulations of this invention may also advantageously employ one or more stabilizing agents including antioxidants. Useful antioxidants include but are not limited to sodium bisulfate, butylated hydroxy toluene (BHT), thiourea, and sodium formaldehyde sulfoxylate.

Preferably, the formulations of the present invention should also achieve a sufficiently high tissue concentration with a minimum number of doses so that a simple dosing regimen can be used to treat or prevent bacterial or parasitic infections. To this end, a preferred technique involves forming or supplying a depot of azalide antibiotic in contact with the superficial tissue. A depot refers to a source of azalide antibiotic that is not rapidly removed by the physiologic clearance mechanisms, e.g., tears, saliva, mucous. This allows for continued, sustained high concentrations of azalide antibiotic to be present in the fluid on the surfaces of the tissue by a single application. In general, it is believed that absorption is dependent on both the dissolved drug concentration and the contact duration of the external tissue with the drug-containing fluid. As the drug is removed by clearance of the fluid and/or absorption into the tissue, more drug is provided, e.g. dissolved, into the replenished fluid from the depot.

Accordingly, the use of a depot more easily facilitates loading of the tissue in view of the typically slow and low penetration rate of the generally or poorly soluble azalide antibiotics. The depot, which retains a bolus of concentrated drug, can effectively slowly "pump" the azalide antibiotic into the tissue. As the azalide antibiotic penetrates the tissue, it is accumulated therein and not readily removed due to its long half-life. As more azalide antibiotic is "pumped" in, the tissue concentration increases and the minimum inhibitory concentration threshold is eventually reached or exceeded, thereby loading the tissue with azalide antibiotic. By significantly exceeding the $MIC_{50}$, more preferably the $MIC_{90}$ level, provided the toxicity limit is not exceeded, a therapeutically effective concentration will remain active in the tissue for an extended period of time due to the low clearance rate of the azalide antibiotic from the tissue. Thus, depending on the depot, one or two applications may provide a complete dosing regimen. Indeed, such a simple dosing regimen may provide a 6 to 14 day treatment concentration within the ocular tissue. A preferred dosing regimen involves one to two doses per day over a one to three day period, more preferably one or two doses in a single day, to provide in vivo at least a 6 day treatment and more typically a 6 to 14 day treatment.

A depot can take a variety of forms so long as the azalide antibiotic can be provided in sufficient concentration levels therein and is releasable therefrom, and that the depot is not readily removed from the tissue. A depot generally remains for at least about 30 minutes after administration, preferably at least 2 hours, and more preferably at least 4 hours. The term "remains" means that neither the depot composition nor the azalide antibiotic is exhausted or cleared from the tissue prior to the indicated time. In some embodiments, the depot can remain for up to eight hours or more. Typical ophthalmic depot forms include aqueous polymeric suspensions, ointments, and solid inserts. Polymeric suspensions are the most preferred form for the present invention.

A preferred form of the azalide formulations for administration of azalide antibiotics to the ocular, nasal, pulmonary, periocular, dermal, buccal, vaginal or otic tissues is an aqueous polymeric suspension. Here, at least one of the azalide antibiotic or the polymeric suspending agent is suspended in an aqueous medium having the properties as described above. The azalide antibiotic may be in suspension, although in the preferred pH ranges the azalide antibiotic will be in solution (water soluble), or both in solution and in suspension. It is possible for significant amounts of the azalide antibiotic to be present in suspension. The polymeric suspending agent is preferably in suspension (i.e. water insoluble and/or water swellable), although water soluble suspending agents are also suitable for use with a suspension of the azalide antibiotic. The suspending agent serves to provide stability to the suspension and to increase the residence time of the dosage form on the tissue. It can also enhance the sustained release of the drug in terms of both longer release times and a more uniform release profile.

Examples of polymeric suspending agents include dextrans, polyethylene glycols, polyvinylpyrolidone, polysaccharide gels, Gelrite™, cellulosic polymers like hydroxypropyl methylcellulose, and carboxy-containing polymers such as polymers or copolymers of acrylic acid, as well as other polymeric demulcents. A preferred polymeric suspending agent is a water swellable, water insoluble polymer, especially a crosslinked carboxy-containing polymer.

Crosslinked carboxy-containing polymers used in practicing this invention are, in general, well known in the art. In a preferred embodiment such polymers may be prepared from at least about 90%, and preferably from about 95% to about 99.9% by weight, based on the total weight of monomers present, of one or more carboxy-containing monoethylenically unsaturated monomers (also occasionally referred to herein as carboxy-vinyl polymers). Acrylic acid is the preferred carboxy-containing monoethylenically unsaturated monomer, but other unsaturated, polymerizable carboxy-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers may be crosslinked by a polyfunctional crosslinking agent, preferably a difunctional crosslinking agent. The amount of crosslinking should be sufficient to form insoluble polymer particles, but not so great as to unduly interfere with sustained release of the azalide antibiotic. Typically the polymers are only lightly crosslinked. Preferably the crosslinking agent is contained in an amount of from about 0.01% to about 5%, preferably from about 0.1% to about 5.0%, and more preferably from about 0.2% to about 1%, based on the total weight of monomers present. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallymethacrylamide and the like. Also included are polyalkenyl polyether crosslinking agents containing two or more alkenyl ether groupings per molecule, preferably alkenyl ether groupings containing terminal $H_2C{=}C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053, the entire contents of which are incorporated herein by reference. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products of isocyanate terminated prepolymers derived from polyester diols, polyether diols or polysiloxane diols with hydroxyalkylmethacrylates, and the like, can also be used as the crosslinking agents; see Mueller et al. U.S. Pat. Nos. 4,192,827 and 4,136,250, the entire contents of each patent being incorporated herein by reference.

The crosslinked carboxy-vinyl polymers may be made from a carboxy-vinyl monomer or monomers as the sole monoethylenically unsaturated monomer present, together with a crosslinking agent or agents. Preferably the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers.

Particularly preferred polymers are lightly crosslinked acrylic acid polymers wherein the crosslinking monomer is 2,3-dihydroxyhexa-1,5-diene or 2,3-dimethylhexa-1,5-diene. Preferred commercially available polymers include polycarbophil (Noveon AA-1) and Carbopol™. Most preferably, a carboxy-containing polymer system known by the tradename DuraSite®, containing polycarbophil, which is a sustained release topical delivery system is used in the aqueous polymeric suspension composition of the present invention.

The crosslinked carboxy-vinyl polymers used in practicing this invention are preferably prepared by suspension or emulsion polymerizing the monomers, using conventional free radical polymerization catalysts, to a dry particle size of not more than about 25 μm in equivalent spherical diameter; i.e., to provide dry polymer particles ranging in size from about 1 to about 25 μm, preferably from about 3 to about 20 μm, and more preferably 1 μm to 10 μm in equivalent spherical diameter. In general, such polymers will have a molecular weight which has been variously reported as being from about 250,000 to about 4,000,000, and from 3,000,000,000 to 4,000,000,000. Using polymer particles that were obtained by mechanically milling larger polymer particles to this size is preferably avoided.

In a more preferred embodiment of the invention for topical administration, the particles of crosslinked carboxy-vinyl polymer are monodisperse, meaning that they have a dry particle size distribution such that at least 80% of the particles fall within a 10 μm band of major particle size distribution. More preferably, at least 90% and most preferably at least 95%, of the particles fall within a 10 μm band of major particle size distribution. Also, a monodisperse particle size means that there is no more than 20%, preferably no more than 10%, and most preferably no more than 5% particles of a size below 1 μm. The use of monodispersed particles will give maximum viscosity and an increased eye residence time of the ophthalmic medicament delivery system for a given particle size. Monodisperse particles having a dry particle size of 10 μm and below are most preferred. Good particle packing is aided by a narrow particle size distribution.

The aqueous polymeric suspension normally contains azalide antibiotics in an amount from about 0.05% to about 25%, preferably about 0.1% to about 20%, more preferably about 0.5% to about 15%, more preferably about 1% to about 12%, more preferably about 2% to about 10.0%, and polymeric suspending agent in an amount from about 0.05% to about 10%, preferably about 0.1% to about 5% and more preferably from about 0.1% to about 1.0% polymeric suspending agent. In the case of the above described water insoluble, water-swellable crosslinked carboxy-vinyl polymer, another preferred amount of the polymeric suspending agent is an amount from about 0.5% to about 2.0%, preferably from about 0.5% to about 1.2%, and in certain embodiments from about 0.5% to about 1.0%, based on the weight of the composition. Although referred to in the singular, it should be understood that one or 25 more species of polymeric suspending agent, such as the crosslinked carboxy-containing polymer, can be used with the total amount falling within the stated ranges. In one preferred embodiment, the composition contains about 0.5% to about 1.0% of the polymeric suspending agent such as Noveon AA-1 (polycarbophil).

In one embodiment, the amount of insoluble lightly crosslinked carboxy-vinyl polymer particles, the pH, and the osmolality can be correlated with each other and with the degree of crosslinking to give a composition having a viscosity in the range of from about 50 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm (Brookfield Engineering Laboratories Inc.; Middleboro, Mass.). Alternatively, when the viscosity is within the range of 500 to 3000 centipoise, it may be determined by a Brookfield Model DV-11+, choosing a number cp-52 spindle at 6 rpm.

When water soluble polymers are used as the suspending agent, such as hydroxypropyl methylcellulose, the viscosity will typically be about 10 to about 400 centipoise, more typically about 10 to about 200 centipoises or about 10 to about 25 centipoise.

A further aspect of the present invention involves the use of additional medicaments in combination with the azalide antibiotic. A composition comprising a concentrated azalide antibiotic, an additional medicament, and a pharmaceutically acceptable carrier can advantageously simplify administration and allow for treating or preventing multiple conditions or symptoms simultaneously. The "additional medicaments," which can be present in any of the compositional forms described herein including fluid and solid forms, are pharmaceutically active compounds having efficacy in topical applications and which are compatible with an azalide antibiotic and with the particular target tissue. Typically, the additional-medicaments include other antibiotics (an antibiotic that is different than an azalide antibiotic), antivirals, antifungals, anesthetics, anti-inflammatory agents, including steroidal and non-steroidal anti-inflammatories, and anti-allergic agents.

Examples of suitable medicaments include aminoglycosides such as amikacin, gentamycin, tobramycin, streptomycin, netilmycin, and kanamycin; fluoroquinolones such as gatifloxacin, moxifloxacin, ciprofloxacin, norfloxacin, ofloxacin, trovafloxacin, lomefloxacin, levofloxacin, and telithromycin, enoxacin; naphthyridine; sulfonamides; polymyxin; chloramphenicol; neomycin; paramomomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; comolyn; lodoxamide; levocabastin; naphazoling; antazoline; and pheniramimane. These other medicaments are generally present in a pharmaceutically effective amount as is understood by workers of ordinary skill in the art. These amounts are generally within the range of from about 0.01 to 5%, more typically 0.1 to 2%, for fluid formulations and from 0.5 to 50% for solid dosage forms.

The steroidal anti-inflammatory agents of the present invention include glucocorticoids, such as dexamethasone, loteprednol, rimexolone, prednisolone, prednisolone acetate, fluticasone propionate, busesonide, triamcinolone, beclomethasone, mometasone furoate, fluorometholone, and hydrocortisone. Dexamethasone derivatives such as U.S. Pat. No. 5,223,493, herein incorporated by reference, may also be used. Particular compounds include "21-ether derivatives of dexamethasone", such as a 21-benzyl ether derivatives of dexamethasone."

The preferred non-steroidal anti-inflammatory agents are: diclofenac, flurbiprofen, ketorolac, and suprofen. Other non-steroidal anti-inflammatory agents useable in the present invention include: prostaglandin H synthetase inhibitors (Cox I or Cox II), also referred to as cyclooxygenase type I and type II inhibitors, such as nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, NCX-4016, HCT-1026, NCX-284, NCX-456, tenoxicam and carprofen; cyclooxygenase type II selective inhibitors, such as NS-398, vioxx, celecoxib, P54, etodolac, L-804600 and S-33516; PAF antagonists, such as SR-27417, A-137491, ABT-299, apafant, bepafant, minopafant, E-6123, BN-50727, nupafant and modipafant; PDE IV inhibitors, such as ariflo, torbafylline, rolipram, filaminast, piclamilast, cipamfylline, CG-1088, V-11294A, CT-2820, PD-168787, CP-293121, DWP-205297, CP-220629, SH-636, BAY-19-8004, and roflumilast; inhibitors of cytokine production, such as inhibitors of the NFkB transcription factor; or other anti-inflammatory agents known to those skilled in the art.

The concentrations of the anti-inflammatory agents contained in the formulations of the present invention will vary based on the agent or agents selected and the type of inflammation being treated. The concentrations will be sufficient to reduce inflammation in the targeted tissues following topical application of the formulations to those tissues. Such an amount is referred to herein as "an anti-inflammatory effective amount". The formulations of the present invention may contain one or more anti-inflammatory agents in an amount of from about 0.01 to about 5% or in a range of from about 0.1 to about 2%, as discussed above for the additional medicaments, or in a range of from about 0.01 to about 1.0 wt. %.

The concentrated azalide antibiotic formulations of the instant invention are preferably formulated for administration via topical administration. The formulations can be administered to humans and a variety of non-human animals, the latter including but not limited to cows, sheep, horses, pigs, goats, rabbits, dogs, cats, and other mammals.

1. Otic Formulations

Examples of otic conditions that may be treated with the formulations of the present invention include otitis externa and otitis media, ear inflammation, ear infections and ear trauma. Examples of bacteria believed to act as pathogens in acute otitis externa infections include "corneforms" or "idphtheroids". They have previously been identified as being present both in healthy ears and in ears afflicted with acute otitis externa infections.

With respect to the treatment of otitis media, the formulations of the present invention may be useful in cases where the tympanic membrane has ruptured or tympanostomy tubes have been implanted. The formulations may also be used to treat infections associated with otic surgical procedures, such as tympanostomy, or to prevent such infections which is acute otitis media with a tympanostomy tube (AOMT). Additionally, the formulations and methods of the present invention may be useful in the treatment of acute infections of the external ear canal, which are commonly referred to as "acute otitis externa" or "AOE". The antibiotics utilized in the present invention have a high level of antimicrobial activity against otic pathogens, and therefore may be useful in the treatment of acute otitis externa infections involving these pathogens.

The azalide antibiotic can be supplied to otic tissue in a variety of ways, including as an aqueous otic solution or suspension. Any delivery technique and any topical otic composition containing a dosage form that supplies an azalide antibiotic to otic tissues is included within the notion of topically applying, although the external surface of the ear is typically the ear canal.

The prevention of infection preferably includes pre-operative treatment prior to surgery as well as other suspected infectious conditions or contact, for example. Examples of prophylaxis situations include treatment prior to surgical procedures and other operative procedures involving ear trauma or ear damage. Topical application of azalide antibiotic can be used to treat acute otitis externa and acute otitis media with a tympanostomy.

Generally, the inventive azalide antibiotic formulations can be used to treat or prevent infections caused by a variety of bacteria or parasites, including but not limited to one or more of the following organisms: *Staphylococcus* including *Staphylococcus aureus* and *Staphylococcus epidermidis; Streptococcus* including *Streptococcus pneumoniae* and *Streptococcus pyogenes* as well as *Streptococci* of Groups C, F, and G and Viridans group of *Streptococci; Haemophilus* influenza including biotype III (*H. Aegyptius*); *Haemophilus ducreyi; Moraxella catarrhalis; Neisseria* including *Neisseria gonorrhoeae* and *Neisseria meningitidis; Chlamydia* including *Chlamydia trachomatis, Chlamydia psittaci*, and *Chlamydia pneumoniae; Mycobacterium* including *Mycobacterium tuberculosis* and *Mycobacterium avium*-intracellular complex as well as a typical *mycobacterium* including *M. marinum, M. fortuitm*, and *M. chelonae; Bordetella pertussis; Campylobacter jejuni; Legionella pneumophila; Bacteroides bivius; Clostridium perfringens; Peptostreptococcus* species; *Borrelia burgdorferi; Mycoplasma pneumoniae; Treponema pallidum; Ureaplasma urealyticum; toxoplasma; malaria*; and *nosema.*

For otic formulations, a viscosity in the range of from about 10 to 1000 centipoise is useful for a drop. Preferably about 50 to about 500 centipoise, more preferably about 50 to about 400 and most preferably about 50 to about 150 centipoise. The use of viscosity enhancing agents to provide the formulations of the invention with viscosities greater than the viscosity of simple aqueous solutions may be desirable to increase absorption of the active compounds by the target tissues or to increase the retention time in the ear, for example.

Aqueous polymeric suspensions of the present invention may be formulated so that they retain the same or substantially the same viscosity before and after administration. Because of the higher viscosity of the formulation, the administered dose is retained at the affected site for a longer period of time. This affords the azalide antibiotic to be released into the affected tissue over a longer period of time. All these events eventually lead to increased patient comfort and increased azalide antibiotic contact time with the tissues, thereby increasing the extent of drug absorption and duration of action of the formulation.

The agents contained in these drug delivery systems will be released from the gels at rates that depend on such factors as the molecular weight of the drug, its ionization state, the extent of drug loading and the pH of the system, as well as on any drug delivery adjuvants, such as ion exchange resins compatible with the otic surface, which may also be present.

The preferred otic azalide formulations disclosed herein are preferably used to treat *Otitis Media*. The ideal otic formulations should be formulated with a viscosity that is reasonably high to render acceptable residence time at the site of action but at the same time sufficiently low to allow the formulation to penetrate through a tympanic tube upon administration. The preferred concentration of Noveon AA-1 is about 0.5% to about 0.9% to maintain the viscosity in the optimal range. The formulations preferably use a citrate buffer and optionally contain DuraSite® as the delivery vehicle. The preferred formulations have about 2%, about 3% about 4% and about 5% Azithromycin. Moreover, the preferred otic formulations contain an anti-inflammatory agent such as dexamethasone. In this case the preferred anti-inflammatory agent is dexamethasone in the range of 0.01 to 1%. In addition to Azithromycin content, the preferred formulations have a pH of about 6 to about 7, preferably about 6.8 to about 6.2 and most preferably 6.3±0.1; osmolality of about 250 to about 330 mOsm/kg, preferably about 270 to about 330 mOsm/kg and most preferably about 300 mOsm/kg, and viscosity of about 10 to about 200 cps, preferably about 50 to about 150 and most preferably about 70 to about 130 cps.

2. Ocular Formulations

Any delivery technique and ocular dosage form that applies an azalide antibiotic to the external eye surface is included within the definition of "topically applying." Although the external surface of the eye is typically the outer layer of the conjunctiva, it is possible that the sclera, cornea, or other ocular tissue could be exposed such as by rotation of the eye or by surgical procedure, and thus be an external surface. For the purposes of this application, periocular tissues are defined as those tissues in contact with the lachrymal secretions, including the inner surface of the eye lid, the tissues of the orbit surrounding the eye, and the tissues and ducts of the lachrymal gland.

Generally a single application, such as one or two drops, provides a therapeutically effective concentration (i.e. one that retards or suppresses the infection) of the azalide antibiotic within a tissue. Indeed, although dependent on the amount and form of the ophthalmic composition, a single application will typically provide a therapeutically effective amount of the azalide antibiotic within a tissue for at least about 2, more preferably about 4, more preferably about 8, more preferably about 12, and more preferably at least about 18 hours.

Azalide antibiotic formulations of this invention can be used to treat or prevent a variety of conditions associated with ocular infection. For example, conditions of the eyelids, including blepharitis, blepharconjunctivies, meibomianitis, acute or chronic hordeolum, chalazion, dacryocystitis, dacryoadenities, and acne rosacea; conditions of the conjunctiva, including conjunctivitis, ophthalmia neonatorum, and trachoma; conditions of the cornea, including corneal ulcers, superficial and interstitial keratitis, keratoconjunctivitis, foreign bodies, and post operative infections; and conditions of the anterior chamber and uvea, including endophthalmitis, infectious uveitis, and post operative infections, are a few of the tissues and conditions that can be treated by topical application of an azalide antibiotic. The prevention of infection includes pre-operative treatment prior to surgery as well as other suspected infectious conditions or contact. Examples of prophylaxis situations include treatment prior to surgical procedures such as blepharoplasty, removal of chalazia, tarsorrhapy, procedures for the canualiculi and lacrimal drainage system and other operative procedures involving the lids and lacrimal apparatus; conjunctival surgery including removal of ptyregia, pingueculae and tumors, conjunctival transplantation, traumatic lesions such as cuts, burns and abrasions, and conjunctival flaps; corneal surgery including removal of foreign bodies, keratotomy, and corneal transplants; refractive surgery including photorefractive procedures; glaucoma surgery including filtering blebs; paracentesis of the anterior chamber; iridectomy; cataract surgery; retinal surgery; and procedures involving the extra-ocular muscles. The prevention of ophthalmia neonatorum is also envisaged.

About 30,000 to about 100,000 centipoise is an advantageous viscosity range for ophthalmic administration in ribbon form. Alternatively, a viscosity in the range of from about 1,000 to 30,000 centipoise is useful for a drop. Preferably about 1200 to about 20,000 centipoise, more preferably about 1500 to about 10,000 and most preferably about 1500 centipoise.

Depot of the azalide antibiotic can be formed by several means within the eye. In one preferred embodiment a depot for topical administration can be formed by including lightly crosslinked carboxyl containing polymers in the formulation, which causes the solution to undergo a rapid increase in viscosity upon a pH rise associated with administration to tissues such as those of the eye and surrounding region. In another embodiment, a depot of the azalide antibiotic can be formed by injection of a bolus of the antibiotic composition into an eye. In one preferred method of ophthalmic administration the injection is intended to form a depot of material within the sclera, to accommodate extended release of the material to the surrounding tissues. Methods of intrascleral administration are discussed in U.S. patent application Ser. No. 09/127,920, filed Aug. 3, 1998 now U.S. Pat. No. 6,378,526 and copending U.S. patent application Ser. No. 09/366,072, filed Aug. 2, 1999, now U.S. Pat. No. 6,397,849. Other means of forming depot include the use of inserts loaded with a bolus of the drug to be delivered. Inserts placed under the eyelid have been used for example to deliver therapeutics to the ocular and periocular region.

In a preferred embodiment where the concentrated azalide antibiotic formulation containing DuraSite® or other similar polyacrylic acid-type polymer at a pH of about 6 to about 6.8, or more preferably about 6.0 to about 6.5, or more preferably at a pH of about 6.2 to about 6.4, or more preferably about 6.25 to about 6.35, or more preferably about 6.3 is administered to the eye, the polymer will swell upon contact with tear fluid which has a higher pH. This gelation or increase in gelation leads to entrapment of the azalide antibiotic in the gel thereby extending the residence time of the composition in the eye if the antibiotic is in solution. If the azalide antibiotic is retained in the gel polymer matrix, the antibiotic is released slowly to the affected tissue over time. All these events eventually lead to increased patient comfort and increased azalide antibiotic contact time with the eye tissues, thereby increasing the extent of drug absorption and duration of action of the formulation in the eye. These antibiotics, display minimal degradation and relatively high solubility in aqueous formulations at the pre-administration pH, with the advantages of the gelling composition.

The viscous gels that result from fluid eye drops typically have residence times in the eye ranging from about 2 to about 4 hours, e.g., from about 2 to about 3 hours. The agents contained in these drug delivery systems will be released from the gels at rates that depend on such factors as the molecular weight of the drug, its ionization state, the extent of drug loading and the pH of the system, as well as on any drug delivery adjuvants, such as ion exchange resins compatible with the ocular surface, which may also be present.

The preferred ophthalmic azalide formulations have about 2%, about 3%, about 4% and about 5% Azithromycin with DuraSite® as the delivery vehicle. Such formulations are intended for the treatment of bacterial conjunctivitis. The formulations preferably use a citrate buffer and optionally contain DuraSite® as the delivery vehicle. Moreover, the preferred ophthalmic formulations contain an anti-inflammatory agent such as dexamethasone. In addition to Azithromycin content, the preferred formulations have a pH of about 6 to about 7, preferably about 6.8 to about 6.2 and most preferably 6.3±0.2; osmolality of about 300 mOsm/kg, preferably about 250 to about 330 mOsm/kg and most preferably 300 mOsm/kg, and viscosity of about 1000 to about 5000 cps, preferably about 1000 to about 2000 cps and most preferably about 1500 cps.

3. Dermal Formulations

In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials. Various cosolvents can be used as known in the art to disperse the components and maintain the components in solution or suspension. The vehicles used for formulations for treating mucosa are limited primarily by the toxicity of the vehicle to the tissue. The vehicle is an important component of some topical formulations, because it can be selected to enhance penetration, to prolong the duration of activity, or to meet requirement of the site of application. For example, a formulation for application to the callous parts of the body, such as the palms of the hand or bottoms of the feet, can include a penetration enhancing agent such as dimethylsulfoxide, propylene glycol or AZONE™.

The preferred dermal azalide antibiotic formulations disclosed herein are preferably used to treat infections of the skin. The dermal formulations are formulated with a higher viscosity in order to be able to stay on the skin surface. The dermal formulation could be in the form of a lotion, ointment or cream. The preferred formulations have about 2%, about 3%, about 4% and about 5% Azithromycin. The formulations preferably use a citrate buffer and optionally contain a polymer such as polycarbophil as the delivery vehicle. Moreover, the preferred dermal formulations contain an anti-inflammatory agent such as dexamethasone. The formulation may contain structure building agent like Cab-O-Sil. In addition to Azithromycin content, the preferred formulations have a pH of about 6 to about 7, preferably about 6.8 to about 6.2 and most preferably 6.3±0.2; osmolality of about 300 mOsm/kg, preferably about 250 to about 330 mOsm/kg and most preferably 300 mOsm/kg, and viscosity of about 100,000 to about 1,000,000 cps, preferably about 250,000 to about 750,000 cps and most preferably about 5,000,000 cps.

4. Nasal Formulations

The concentrated aqueous azalide formulations of the invention are also envisaged for nasal administration in specific, measured amounts, preferably in the form of an aqueous solution or suspension, by use of a pump spray bottle such as the bottles used to deliver VANCENASE AQ™. The aqueous formulations of the present invention may be prepared by admixing concentrated aqueous azalide formulations with other pharmaceutically acceptable excipients, for example. The aqueous formulations according to the present invention may contain, inter alia, additional water, auxiliaries and/or one or more of the excipients, such as: suspending agents, e.g., microcrystalline cellulose, sodium carboxymethylcellulose, hydroxpropyl-methyl cellulose; humectants, e.g. glycerin and propylene glycol; acids, bases or buffer substances for adjusting the pH, e.g., citric acid, sodium citrate, and; surfactants, e.g. Polysorbate 20, Polysorbate 80, glyceryl monoleate, lecithin, or Poloxamer 407 and antimicrobial preservatives, e.g., benzalkonium chloride, phenylethyl alcohol and potassium sorbate.

The preferred nasal azalide formulations disclosed herein are preferably used to treat infections of the nasopharyngeal passages. The nasal formulations have a lower viscosity in order to be effectively administered to the nasal passages. The preferred formulation have about 2%, about 3%, about 4% and about 5% Azithromycin. The formulations preferably use a citrate buffer and optionally contain DuraSite® or Noveon AA-1 as a suspending/mucoadhesive agent and delivery vehicle. In order to achieve a lower viscosity, the concentration of Noveon AA-1 may be reduced from about 0.5% to about 0.9%. The formulations preferably use a citrate buffer and optionally contain a surfactant such as poloxamer. Moreover, the preferred nasal formulations contain an anti-inflammatory agent such as dexamethasone. In addition, the preferred formulations have a pH of about 6 to about 7, preferably about 6.8 to about 6.2 and most preferably 6.3±0.1; osmolality of about 250 to about 330 mOsm/kg, preferably about 270 to about 330 mOsm/kg and most preferably about 300 mOsm/kg, and viscosity of about 10 to about 200, preferably about 50 to about 150 and most preferably about 70 to about 130 cps.

5. Inhalation Formulations

Preferably, inhalation formulations are useful in delivering azalide antibiotic to the oral airway passages and lungs by oral inhalation or intranasally by inhalation. The inhalation formulations of the present invention may be prepared by admixing concentrated aqueous azalide formulations with other pharmaceutically acceptable excipients, for example. The aqueous formulations according to the present invention may contain, inter alia, additional water, auxiliaries and/or one or more of the excipients, such as acids, bases or buffer substances for adjusting the pH, e.g., hydrochloric acid, sodium hydroxide, citric acid, sodium citrate, sulfuric acid and; surfactants, e.g. Polysorbate 80, sorbitan trioleate, or lecithin and antimicrobial preservatives, e.g., benzalkonium chloride, phenylethyl alcohol and chlorobutanol.

The concentrated aqueous azalide formulations of the invention are also envisaged for inhalational administration in specific, measured amounts, preferably in the form of an aqueous suspension, by use of a nebulizer such as the Pari LC® Plus or the AeroEclipse®. In another embodiment, the concentrated aqueous azalide formulations of the invention are delivered using a metered dose inhaler ('MDI'). An MDI preferably delivers aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents.

The preferred inhalation azalide formulations disclosed herein are preferably used to treat infections of the respiratory system. The inhalation formulations have a lower viscosity in order to be effectively nebulized into inhalation aerosol. The preferred formulation have about 2%, about 3%, about 4% and about 5% Azithromycin. The formulations preferably use a citrate buffer and optionally contain DuraSite® or Noveon AA-1 as a suspending/mucoadhesive agent and delivery vehicle. In order to achieve a lower viscosity, the concentration of Noveon AA-1 may be reduced from about 0.5% to about 0.9%. The formulations preferably use a citrate buffer and optionally contain a surfactant such as Polysorbate 80. Moreover, the preferred inhalation formulations contain an anti-inflammatory agent such as dexamethasone. In addition, the preferred formulations have a pH of about 6 to about 7, preferably about 6.8 to about 6.2 and most preferably 6.3±0.1; osmolality of about 250 to about 330 mOsm/kg, preferably about 270 to about 330 mOsm/kg and most preferably about 300 mOsm/kg, and viscosity of about 10 to about 200, preferably about 50 to about 150 and most preferably about 70 to about 130 cps.

6. Buccal Formulations

The invention also includes topical buccal formulations. Preferably such formulations are for application to the oral mucosa, which includes the oral cavity, oral epithelium, palate, gingival, and the nasal mucosa. In embodiments of the invention, the oral composition is preferably an aqueous composition applied to the tooth surface either alone or in combination with mechanical application. One embodiment of the invention includes a component that reduces or minimizes an unpleasant organoleptic property of the compound. This may include a bitter taste in the mouth or throat, or an unpleasant sensation in the nose. The invention is thus further directed to a process of treating tissue or applying an active agent to an area with little or no irritation. It has been found that various natural and particularly artificial or synthetic non-nutritive sweeteners are able to provide a temporary suppression of pain and irritation to the area being treated when applied topically.

Preferably, the buccal formulations include a carrier that is solid or semi-solid at room temperature and is capable of releasing the azalide antibiotic to the delivery area in the mouth. In embodiments of the invention, suitable solid carriers included sucrose, corn syrup solids, and other confectionery formulations. The carrier may for example, be a lozenge, hard candy, lollipop or gel and the like comprising an azalide antibiotic. Preferably, they also have either a natural or artificial sweetener. Preferably, the solid carrier is water soluble that can dissolve in the mouth to release the active agent and anti-irritant. Preferred natural sweeteners include sorbitol, mannitol and xylitol.

Examples of semi-solid carriers include gels, chewing gums and other chewable compositions and compositions as known in the art. The carrier can be a conventional toothpaste or dentifrice gel. In one embodiment of the invention, the composition is in the form of a chewing gum comprising a chewing gum base and an azalide antibiotic. Oral formulations may also contain an effective amount of a fluoride to treat the tooth surfaces.

The chewing gum base of the invention can be a conventional gum base as known in art that can contain one or more solvents, plasticizer, flavorants and colorants. The composition generally contains up to about 50% by weight of a gum base based on the total weight of the composition. Suitable chewing gum bases include natural and synthetic elastomers and rubbers. Natural chewing gum bases include natural rubber, chickle, jeluting, gutta percha and croun gum. Other gum bases includes resins, such as comatone resin, pontianak resin, copel gum, kauri gum, dammar gum, sweet bay gum, spruce gum, and balsams. Synthetic elastomers includes butadiene-styrene copolymers, isobutylene-isoprene copolymers, polyethylene, polyisobutylene, polyvinylacetate and copolymers of vinyl acetate.

The preferred buccal/peridontal azalide formulations disclosed herein are used to treat infections of the mouth. The buccal formulations have a higher viscosity in order to be retained in the mouth. The preferred formulations have about 2%, about 3%, about 4% and about 5% Azithromycin. The formulations preferably use a citrate buffer and optionally contain a surfactant such as poloxamer, and a polymer such as polycarbophil as a suspending and mucoadhesive agent. Moreover, the preferred buccal formulations contain an anti-inflammatory agent such as dexamethasone. The preferred formulations have a pH of about 6 to about 7, preferably about 6.8 to about 6.2 and most preferably 6.3±0.2; osmolality of about 300, preferably about 250 to about 330 mOsm/kg and most preferably 300 mOsm/kg, and viscosity of about 50,000 to about 1,000,000 cps, preferably about 100,000 to about 500,00 cps and most preferably about 250,000 cps. See for Example Table 6.

All of the percentages recited herein refer to weight percent, unless otherwise indicated. The following non-limiting examples serve to illustrate certain features of the present invention.

EXAMPLE 1

Ophthalmic Formulations Made at the 12 L Scale

In a first step, EDTA, sodium chloride and Noveon (Solution #1) are mixed for 30 minutes using an overhead mixer. The solution is then transferred to a stainless steel pressure can. The solution is transferred using pressure through a 100 mesh screen into the 12 L vessel. In the second step, sodium hydroxide is added to the vessel containing Solution #1. The volume of sodium hydroxide required is based upon targeting a final batch pH of 6.3. This solution is sterilized within the tank at 121.1° C. for 30 minutes. The stainless steel pressure can and transfer line are then rinsed with house DI water. In a third step, mannitol, citric acid, sodium citrate, hydrochloric acid, azithromycin, benzalkonium chloride (BAC), and Poloxamer 407 (Solution #2) are mixed together. Hydrochloric acid is added to facilitate the dissolution of azithromycin. After all of the solid components in Solution #2 are fully dissolved, it is transferred aseptically into the 12 L vessel through a 0.2 μm filter. Alternatively, the sodium hydroxide may be added as the last step to insure a pH of 6.3 is achieved. The stainless steel pressure can and filter are then rinsed with DI water and the rinsate is added aseptically to the solution in the 12 L vessel. The rinse volume is determined by targeting a final batch volume of 12 liters. See Table 1.

EXAMPLE 2

Otic Formulations Made at the 12 L Scale

In a first step, EDTA, sodium chloride and Noveon AA-1 (Solution #1) are mixed for 30 minutes using an overhead mixer. The solution is then transferred to a stainless steel pressure can. The solution is transferred using pressure through a 100 mesh screen into the 12 L vessel. In the second step, sodium hydroxide is added to the vessel containing Solution #1. The volume of sodium hydroxide required is based upon targeting a final batch pH of 6.3. This solution is sterilized within the tank at 121.1° C. for 30 minutes. The stainless steel pressure can and transfer line are then rinsed with DI water. In a third step, mannitol, citric acid, sodium citrate, hydrochloric acid, azithromycin, BAC, and Poloxamer 407 (Solution #2) are mixed together. Hydrochloric acid is added to facilitate the dissolution of azithromycin. After all of the solid components in Solution #2 are fully dissolved, it is transferred aseptically into the 12 L vessel through a 0.2 μm filter. Alternatively, the sodium hydroxide may be added as the last step to insure a pH of 6.3 is achieved. The stainless steel pressure can and filter are then rinsed with DI water and the rinsate is added aseptically to the solution in the 12 L vessel. The rinse volume is determined by targeting a final batch volume of 12 liters. See Table 2.

EXAMPLE 3

Nasal Formulations Made at the 12 L Scale

In a first step, EDTA, sodium chloride and Noveon AA-1 (Solution #1) are mixed for 30 minutes using an overhead mixer. The solution is then transferred to a stainless steel pressure can. The solution is transferred using pressure through a 100 mesh screen into the 12 L vessel. In the second step, sodium hydroxide is added to the vessel containing Solution #1. The volume of sodium hydroxide required is based upon targeting a final batch pH of 6.3. This solution is sterilized within the tank at 121.1° C. for 30 minutes. The stainless steel pressure can and transfer line are then rinsed with DI water. In the third step, dexamethasone, Polysorbate 80, citric acid, sodium citrate, hydrochloric acid, azithromycin, BAC, and Poloxamer 407 (Solution #2) are mixed together. Hydrochloric acid is added to facilitate the dissolution of azithromycin. After all of the solid components in Solution #2 are fully dissolved, it is transferred aseptically into the 12 L vessel through a 0.2 μm filter. The stainless steel pressure can and filter are then rinsed with DI water and the rinsate is added aseptically to the solution in the 12 L vessel. Alternatively, the sodium hydroxide may be added as the last step to insure a pH of 6.3 is achieved. The rinse volume is determined by targeting a final batch volume of 12 liters. See Table 3

EXAMPLE 4

Inhalation Formulations Made at the 12 L Scale

In a first step, EDTA, sodium chloride and Noveon AA-1 (Solution #1) are mixed for 30 minutes using an overhead mixer. The solution is then transferred to a stainless steel pressure can. The solution is transferred using pressure through a 100 mesh screen into the 12 L vessel. In the second step, sodium hydroxide is added to the vessel containing Solution #1. The volume of sodium hydroxide solution required is based upon targeting a final batch pH of 6.3. This solution is sterilized within the tank at 121.1° C. for 30 minutes. The stainless steel pressure can and transfer line are then rinsed with DI water. In the third step, dexamethasone, Polysorbate 80, citric acid, sodium citrate, hydrochloric acid, azithromycin, and BAC, (Solution #2) are mixed together. Hydrochloric acid is added to facilitate the dissolution of Azithromycin. After all of the solid components in Solution #2 are fully dissolved, it is transferred aseptically into the 12 L vessel through a 0.2 μm filter. The stainless steel pressure can and filter are then rinsed with DI water and the rinsate is added aseptically to the solution in the 12 L vessel. Alternatively, the sodium hydroxide may be added as the last step to insure a pH of 6.3 is achieved. The rinse volume is determined by targeting a final batch volume of 12 liters. See Table 4.

EXAMPLE 5

Dermal Formulations Made at the 12 L Scale

In a first step, EDTA, sodium chloride, Cabosil, and Noveon AA-1 (Solution #1) are mixed for 30 minutes using an overhead mixer. The solution is then transferred to a stainless steel pressure can. The solution is transferred using pressure through a 100 mesh screen into the 12 L vessel. In the second step, sodium hydroxide is added to the vessel containing Solution #1. The volume of sodium hydroxide solution required is based upon targeting a final batch pH of 6.3. This solution may or may not be sterilized within the tank at 121.1° C. for 30 minutes. The stainless steel pressure can and transfer line are then rinsed with DI water. In the third step, dexamethasone, Polysorbate 80, citric acid, sodium citrate, hydrochloric acid, azithromycin, BAC, and Poloxamer 407 (Solution #2) are mixed together. Hydrochloric acid is added to facilitate the dissolution of Azithromycin. After all of the solid components in Solution #2 are fully dissolved, it is transferred either non-aseptically or aseptically through a 0.2 μm filter into the 12 L vessel. The stainless steel pressure can and filter are then rinsed with DI water and the rinsate is added either aseptically or non-aseptically to the solution in the 12 L vessel. Alternatively, the sodium hydroxide may be added as the last step to insure a pH of 6.3 is achieved. The rinse volume is determined by targeting a final batch volume of 12 liters. See Table 5.

In this disclosure there is described only the preferred embodiments of the invention and but a few examples of its versatility. It is to be understood that the invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this invention. All references cited herein are incorporated by reference in their entirety for all purposes.

What is claimed is:

1. A method of making a concentrated aqueous azithromycin formulation comprising from about 2% to 20% azithromycin, said method comprising the steps of:

(a) preparing and sterilizing a first solution comprising a strong base to form a sterilized solution, (b) dissolving the azithromycin in an aqueous solution comprising a strong acid, and (c) adding the aqueous solution comprising the strong acid to the sterilized solution comprising the strong base, wherein the strong acid has a pKa less than about −1.74.

2. The method of claim 1 wherein the strong acid is hydrochloric acid.

3. The method of claim 1 wherein the strong base is sodium hydroxide.

4. The method of claim 1, wherein the aqueous solution further comprises a polymeric agent.

5. The method of claim 4 wherein the polymeric agent is Noveon AA-1.

6. The method of claim 1 wherein the aqueous azithromycin formulation comprises an anti-inflammatory agent.

7. The method of claim 6 wherein the anti-inflammatory agent is a dexamethasone.

8. The method of claim 7, wherein the dexamethasone has a concentration of about 0.1%.

* * * * *